United States Patent
Godard et al.

(10) Patent No.: US 9,090,552 B2
(45) Date of Patent: Jul. 28, 2015

(54) METHOD OF OXIDATIVE MOLECULAR CLEAVAGE OF A FATTY COMPOUND

(71) Applicants: Anais Godard, Toulouse (FR); Sophie Thiebaud Roux, L'union (FR); Pascale De Caro, Toulouse (FR); Emeline Vedrenne, Quint-Fonsegrives (FR); Zephirin Mouloungui, Toulouse (FR)

(72) Inventors: Anais Godard, Toulouse (FR); Sophie Thiebaud Roux, L'union (FR); Pascale De Caro, Toulouse (FR); Emeline Vedrenne, Quint-Fonsegrives (FR); Zephirin Mouloungui, Toulouse (FR)

(73) Assignees: INSTITUT NATIONAL POLYTECHNIQUE DE TOULOUSE, Toulouse (FR); INSTITUT NATIONAL DE LA RECHERCHE AGRONOMIQUE, Paris (FR)

( * ) Notice: Subject to any disclaimer, the term of this patent is extended or adjusted under 35 U.S.C. 154(b) by 0 days.

(21) Appl. No.: 14/367,351

(22) PCT Filed: Dec. 21, 2012

(86) PCT No.: PCT/FR2012/053037
§ 371 (c)(1),
(2) Date: Jun. 20, 2014

(87) PCT Pub. No.: WO2013/093366
PCT Pub. Date: Jun. 27, 2013

(65) Prior Publication Data
US 2014/0371487 A1    Dec. 18, 2014

(30) Foreign Application Priority Data
Dec. 22, 2011 (FR) .................................. 11 04028

(51) Int. Cl.
*C07C 51/285* (2006.01)
*C07C 53/126* (2006.01)
*C07C 55/08* (2006.01)
*C07C 55/12* (2006.01)
*C07C 55/18* (2006.01)
*C07C 51/347* (2006.01)

(52) U.S. Cl.
CPC ............. *C07C 51/347* (2013.01); *C07C 51/285* (2013.01)

(58) Field of Classification Search
None
See application file for complete search history.

(56) References Cited

FOREIGN PATENT DOCUMENTS

JP    5-004938    1/1993

OTHER PUBLICATIONS

Machine translation of JP 5 004938; published 1993.*
International Search Report, dated Mar. 22, 2013, from corresponding PCT application.
Z.P. Pai et al., "Catalytic oxidation of olefins and alcohols with hydrogen peroxide in a two-phase system giving mono-and dicarboxylic acids", Russian Chemical Bulletin, Aug. 2005, pp. 1847-1854, vol. 54, No. 8.
Jumat Salimon et al., "Oleic Acid Diesters: Synthesis, Characterization and Low Temperature Properties", European Journal of Scientific Research, 2009, pp. 216-222, vol. 32, No. 2.

* cited by examiner

*Primary Examiner* — Yevegeny Valenrod
(74) *Attorney, Agent, or Firm* — Young & Thompson

(57) ABSTRACT

A method of oxidative molecular cleavage of a fatty compound, includes:—forming a liquid composition, referred to as a fatty composition, consisting of at least one aliphatic carboxylic acid, the fatty composition including the fatty compound; characterized in that it then involves:—adding, to the fatty composition, a solution of at least one quaternary ammonium salt in water capable of forming an emulsion from the fatty compound and water, then;—adding, to the emulsion, a liquid solution of at least one tungstophosphoric acid in a composition including hydrogen peroxide ($H_2O_2$), in such a way as to form, in situ in the emulsion, a quantity of a phase-transfer catalyst, formed from tungstophosphoric acid and at least one quaternary ammonium from the quaternary ammonium salt(s), and to allow the oxidative molecular cleavage of the fatty compound.

15 Claims, No Drawings

METHOD OF OXIDATIVE MOLECULAR CLEAVAGE OF A FATTY COMPOUND

The invention relates to a method of preparing carboxylic acids by oxidative molecular cleavage of a fatty compound. In particular, the invention relates to a method of preparing carboxylic acids (especially carboxylic monoacids and/or carboxylic diacids and/or ω-ester carboxylic acids and/or hydroxylated carboxylic acids) by oxidative molecular cleavage of a fatty compound selected from the group formed of unsaturated aliphatic carboxylic acids, esters, in particular alkyl esters, especially methyl esters, of an unsaturated aliphatic carboxylic acid, epoxidized aliphatic carboxylic acids, esters, in particular alkyl esters, especially methyl esters, of an epoxidized aliphatic carboxylic acid, hydroxylated unsaturated aliphatic carboxylic acids, and esters, in particular alkyl esters, especially methyl esters, of a hydroxylated unsaturated aliphatic carboxylic acid.

Such a method of oxidative molecular cleavage of a fatty compound is used in the field of the manufacture of short-chain fatty acids, especially fatty acids having a main chain of less than 12 carbon atoms, and in particular fatty acids having a main chain with an uneven number of carbon atoms.

In addition, these compounds, especially azelaic acid converted in particular into the form of esters, constitute a starting material for the manufacture of many industrial products, especially polymers, such as nylon 6/9, plasticizers, adhesives, solvents, biodegradable lubricants and corrosion inhibitors. In addition, azelaic acid constitutes an active ingredient of cosmetic compositions as a keratolytic compound and as an anti-acne agent. Pelargonic acid is a synthesis intermediate for various lubricants, plasticizers, perfumes, herbicides, fungicides and resins.

Methods which allow the oxidative molecular cleavage of unsaturated fatty acids are already known. Such methods require the use of compounds which are toxic and/or dangerous to human health and/or the environment, such as chromic acid, nitric acid, potassium permanganate, osmium tetroxide, peracids, periodates and hypochlorites. A method is also known in which ozone is used as the oxidizing reagent for the oxidative molecular cleavage of oleic acid to pelargonic acid and azelaic acid.

Such compounds used in a method of oxidative molecular cleavage of a fatty compound are not environmentally friendly.

In addition, the document (Pai et al., (2005), Russian Chemical Bulletin, International Edition, 54; 8, 1847-1854) describes a method of synthesis of azelaic acid and pelargonic acid by catalytic oxidative molecular cleavage of oleic acid in a hydrogen peroxide solution. In such a method, the synthesis of a solid catalyst of the general formula $[C_5H_5N(n-C_{16}H_{33})]_3\{PO_4—[WO(O_2)_2]_4\}$ is first carried out. A quantity of the solid catalyst is then placed in a reactor. Oleic acid is subsequently added, then the resulting mixture is stirred, and then a hydrogen peroxide solution is added and the mixture is heated.

In such a method, therefore, a specific step of synthesis of the catalyst in the absence of oleic acid is first carried out, then said catalyst is purified before the oxidative molecular cleavage of the oleic acid to azelaic acid and pelargonic acid is carried out. Such a method does not allow the synthesis of carboxylic monoacid and diacid to be carried out in a single step. In particular, such a method requires purification of the catalyst. This purification step leads to losses of solid catalyst during its purification. Finally, such a method is complex in that it requires a first step of forming the catalyst, which is to be carried out at ambient temperature, and then a second step of oxidative cleavage of the oleic acid, which is to be carried out at a temperature of 80° C.

The invention aims to remedy the disadvantages described above by proposing a method of oxidative molecular cleavage of a fatty compound which does not require the use of a toxic oxidizing agent. The invention therefore relates to a method of oxidative molecular cleavage of a fatty compound which is environmentally friendly.

The invention relates in particular to such a method of oxidative molecular cleavage of a fatty compound which exhibits an improved yield as compared with the methods of the prior art. In particular, the invention relates to such a method of oxidative molecular cleavage of a fatty compound which is carried out in a single step and which requires only a simple treatment of purification of the oxidative molecular cleavage products of said fatty compound.

The invention relates also to such a method of oxidative molecular cleavage of a fatty compound which is simple to carry out and which does not require the provision of specific or dangerous installations. In particular, the invention relates to such a method of oxidative molecular cleavage of a fatty compound which is carried out at atmospheric pressure.

The invention accordingly relates to such a method of oxidative molecular cleavage of a fatty compound which is eco-compatible, that is to say which does not require for its implementation an organic solvent which is toxic for the environment and/or for human or animal health and which is obtained from fossil resources, especially from oil or natural gas, which are not renewable.

The invention accordingly relates to such a method of oxidative molecular cleavage of a fatty compound obtained from a resource that respects European recommendations in terms of sustainable development.

The invention relates also to such a method of oxidative molecular cleavage of a fatty compound which can be produced from a natural resource, especially from a natural plant resource obtained from agriculture and/or from forestry, which is renewable, such as sunflower oil, which is produced in large quantities in the south of France and in the countries of the Mediterranean region.

The invention relates to such a method of oxidative molecular cleavage of a fatty compound which does not require multiple steps of synthesis and purification of a catalyst of oxidative molecular cleavage.

The invention relates to such a method of oxidative molecular cleavage of a fatty compound which allows the value of a plant resource which is renewable, especially sunflower oil, to be increased.

It is a further aim of the invention to achieve all those objects at lower cost by proposing a method of oxidative molecular cleavage of a fatty compound which has a low cost price and is carried out starting from conventional and inexpensive means, especially organic or mineral compounds.

More particularly, it is a further aim of the invention to propose such a solution which is compatible with the constraints of safety, sustainable development, profitability and respect for the environment.

To that end, the invention relates to a method of oxidative molecular cleavage of a fatty compound selected from the group formed of unsaturated aliphatic carboxylic acids, esters of an unsaturated aliphatic carboxylic acid, epoxidized aliphatic carboxylic acids, esters of an epoxidized aliphatic carboxylic acid, hydroxylated unsaturated aliphatic carboxylic acids, and esters of a hydroxylated unsaturated aliphatic carboxylic acid, wherein:

a composition, called a fatty composition, composed of at least one aliphatic carboxylic acid is formed, said fatty composition comprising the fatty compound; which method comprises:

subsequently adding to said fatty composition a solution of at least one quaternary ammonium salt in water capable of forming an emulsion of said fatty compound and water; and then adding to said emulsion a liquid solution of at least one tungstophosphoric acid in a composition comprising hydrogen peroxide ($H_2O_2$);

so as to form in situ in the emulsion a quantity of a catalyst, called a phase-transfer catalyst, formed of tungstophosphoric acid and at least one quaternary ammonium of the quaternary ammonium salt(s), and to permit the oxidative molecular cleavage of the fatty compound.

The invention therefore consists in proposing a method of oxidative molecular cleavage of a fatty compound, wherein an emulsion of the fatty compound and of an aqueous solution of at least one quaternary ammonium salt is prepared and there are then added to said emulsion at least one tungstophosphoric acid of the formula $H_3PW_{12}O_{40}$ and hydrogen peroxide so as to form in situ in said emulsion a catalyst, called a phase-transfer catalyst, capable of being distributed in the emulsion, and to permit oxidative molecular cleavage of the fatty compound and the formation of carboxylic monoacids and/or carboxylic diacids and/or ω-ester carboxylic acids and/or hydroxylated carboxylic acids. Such a method therefore does not require a step of purification of said phase-transfer catalyst.

The inventors have in fact found that such a method of oxidative molecular cleavage of a fatty compound, wherein the synthesis of a phase-transfer catalyst is carried out in situ in the reaction medium formed of an emulsion of said fatty compound and of an aqueous phase, allows the yield of said oxidation reaction to be increased beyond the oxidative molecular cleavage yield obtained in a comparable oxidative molecular cleavage reaction carried out with a comparable quantity of phase-transfer catalyst prepared in advance with the same quantity of quaternary ammonium salt and of tungstophosphoric acid.

The inventors suppose that a method of oxidative molecular cleavage of a fatty compound according to the invention permits improved dispersion of the phase-transfer catalyst in the emulsion of the fatty compound and water.

Advantageously, the fatty compound is a liquid composition.

Advantageously, each tungstophosphoric acid is a hydrated tungstophosphoric acid of the following general formula (I):

$$H_3PW_{12}O_{40}, nH_2O \quad (I),$$

wherein n is a decimal number.

Advantageously, the tungstophosphoric acid is adapted to form in situ in the emulsion a quantity of a phase-transfer catalyst formed of the tungstophosphoric acid in peroxo form (comprising at least one —O—O— bond) and of each quaternary ammonium.

Advantageously, there is subsequently added to said fatty composition a solution of at least one quaternary ammonium salt in water capable of forming an emulsion of said fatty compound and water.

Advantageously, the fatty composition comprises at least one carboxylic acid selected from the group formed of monounsaturated aliphatic carboxylic acids (for example oleic acid, palmitoleic acid) and polyunsaturated aliphatic carboxylic acids (for example linoleic acid, arachidonic acid).

Advantageously, in a first variant of a method according to the invention, the fatty composition is composed mainly of the fatty compound selected from the group formed of unsaturated aliphatic carboxylic acids, especially oleic acid and linoleic acid, and epoxidized aliphatic carboxylic acids, especially 9,10-epoxyoctadecanoic acid, esters of aliphatic carboxylic acids, especially methyl oleate, and hydroxylated carboxylic acids, especially ricinoleic acid.

Advantageously, in a second variant of a method according to the invention, the fatty composition is composed substantially (apart from optional traces of residual saturated or unsaturated fatty acids) of the fatty compound selected from the group formed of unsaturated aliphatic carboxylic acids, especially oleic acid and linoleic acid, and epoxidized aliphatic carboxylic acids, especially 9,10-epoxyoctadecanoic acid, and esters of aliphatic carboxylic acids, especially methyl oleate.

Advantageously, in a third variant of a method according to the invention, the fatty composition is a mixture comprising at least one fatty compound selected from the group formed of unsaturated aliphatic carboxylic acids, esters of an unsaturated aliphatic carboxylic acid, epoxidized aliphatic carboxylic acids, esters of an epoxidized aliphatic carboxylic acid, hydroxylated unsaturated aliphatic carboxylic acids, especially selected from the group formed of α-hydroxylated unsaturated aliphatic carboxylic acids and β-hydroxylated unsaturated aliphatic carboxylic acids, esters of a hydroxylated unsaturated aliphatic carboxylic acid, and at least one saturated fatty acid or fatty acid ester, especially palmitic acid, an alkyl palmitate (in particular methyl palmitate), stearic acid, an alkyl stearate (in particular methyl stearate), myristic acid, an alkyl myristate (in particular methyl myristate). In general, the fatty composition comprises at least one fatty compound selected from the group formed of unsaturated aliphatic carboxylic acids and their alkyl esters, epoxidized aliphatic carboxylic acids and their alkyl esters, and hydroxylated unsaturated aliphatic carboxylic acids, especially selected from the group formed of α-hydroxylated unsaturated aliphatic carboxylic acids and β-hydroxylated unsaturated aliphatic carboxylic acids, and their alkyl esters, and also comprises a molar fraction of at least one aliphatic carboxylic acid obtained from the hydrolysis—enzymatic or chemical—of at least one triglyceride. Advantageously, the fatty composition is obtained by enzymatic hydrolysis of sunflower oil. By way of example, the fatty acid profile of such a fatty composition obtained by enzymatic hydrolysis of sunflower oil can comprise a proportion by mass of approximately 87% oleic acid, a proportion by mass of approximately 5% linoleic acid, a proportion by mass of approximately 3% palmitic acid, a proportion by mass of approximately 3% stearic acid, a proportion by mass of approximately 0.2% capric acid. In general, such a fatty composition comprises at least one fatty compound selected from the group formed of the unsaturated aliphatic carboxylic acids and the epoxidized aliphatic carboxylic acids, and at least one fatty acid selected from the saturated fatty acids (lauric acid, myristic acid, palmitic acid, stearic acid) and the polyunsaturated fatty acids (oleic acid, linoleic acid, linolenic acid, arachidonic acid).

Advantageously and according to the invention, the fatty compound is selected from the group formed of the fatty compounds of the following general formula (II):

$$R_1-(CH_2)_a-R_2-(CH_2)_b-R_3-(CH_2)_c-R_4-(CH_2)_d-R_5-(CH_2)_e-R_6 \quad (II),$$

wherein:
R₁ and R₆ are two identical or different groups of atoms selected from a methyl (—CH₃), a carboxyl (—COOH) and an ester group of the general formula —COOR₇ wherein R₇ is a linear aliphatic hydrocarbon group containing from 1 to 8 carbon atoms;
R₂, R₃, R₄ and R₅ are identical or different groups of atoms selected from a group —CH₂—, an epoxide group

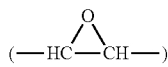

and a group (—CH=CH—);
a, b, c, d and e are identical or different natural integers of the interval [0; 15].

Advantageously, the fatty compound is selected from the group formed of oleic acid, linoleic acid, linolenic acid, arachidonic acid, palmitoleic acid (or 9-cis-hexadecenoic acid), erucic acid (docos-13-enoic acid), brassidic acid (trans-13-dococenoic acid), ricinoleic acid and 9-epoxyoctadecanoic acid.

Advantageously and according to the invention, each quaternary ammonium salt is selected from the group formed of the quaternary ammonium salts of the following general formula (III):

$$A_1A_2A_3A_4N^+X^- \qquad (III),$$

wherein:
A₁, A₂, A₃ and A₄ are identical or different aliphatic hydrocarbon groups having a number of carbon atoms of less than 10; and
X⁻ is an anion, especially selected from the group formed of a chloride, a nitrate and a bromide.

Advantageously, the quaternary ammonium is selected from the group formed of the alkyl-pyridiniums. Advantageously, the quaternary ammonium is the hexadecylpyridinium of the following formula:

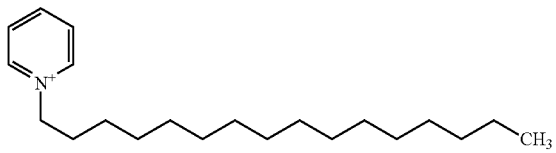 [SMILES: CCCCCCCCCCCCCCCC[n+]1ccccc1]

Advantageously, the quaternary ammonium is selected from the group formed of N,N,N,N-tetrabutylammonium, N,N,N-tributyl-N-methylammonium and N,N,N,N-tetrahexylammonium.

Advantageously and according to the invention, the fatty composition is free of organic solvent. The oxidative molecular cleavage of the fatty compound is carried out in the emulsion formed of the fatty compound and water in the presence of the phase-transfer catalyst formed in situ in the emulsion and without addition of an organic solvent, especially of a volatile organic solvent, selected from the group formed of dichloromethane (CH₂Cl₂), chloroform (CHCl₃), ethyl ether ((H₃C—CH₂)₂O), tert-butanol (ᵗBuOH) and acetonitrile (CH₃CN).

Advantageously and according to the invention, the fatty compound is oleic acid ((9cis)-octadec-9-enoic acid) and the products formed by oxidative molecular cleavage of the oleic acid are azelaic acid (HOOC—(CH₂)₇—COOH) and pelargonic acid (H₃C—(CH₂)₇—COOH).

Advantageously and according to the invention, the fatty compound is linoleic acid ((9cis,12cis)-octadeca-9,12-dienoic acid) and the products formed by oxidative molecular cleavage of the linoleic acid are azelaic acid (nonane-1,9-dioic acid, HOOC—(CH₂)₇—COOH), malonic acid (1,3-propanedioic acid, HOOC—CH₂—COOH) and hexanoic acid (H₃C—(CH₂)₄—COOH).

Advantageously and according to the invention, the fatty compound is 9,10-epoxyoctadecanoic acid and the products formed by oxidative molecular cleavage of the 9,10-epoxyoctadecanoic acid are azelaic acid (nonane-1,9-dioic acid, HOOC—(CH₂)₇—COOH) and pelargonic acid (H₃C—(CH₂)₇—COOH).

Advantageously and according to the invention, the fatty compound is arachidonic acid and the products formed by oxidative molecular cleavage of the arachidonic acid are hexanoic acid (H₃C—(CH₂)₄—COOH), malonic acid (HOOC—CH₂—COOH) and pentanedioic acid (HOOC—(CH₂)₃—COOH).

Advantageously and according to the invention, the fatty compound is palmitoleic acid and the products formed by oxidative molecular cleavage of the palmitoleic acid are azelaic acid (HOOC—(CH₂)₇—COOH) and heptanoic acid (H₃C—(CH₂)₅—COOH).

Advantageously and according to the invention, the fatty compound is erucic acid (or docos-13-enoic acid) and the products formed by oxidative molecular cleavage of the erucic acid are pelargonic acid (H₃C—(CH₂)₇—COOH) and 1,13-tridecanedioic acid (HOOC—(CH₂)₁₁—COOH).

Advantageously and according to the invention, the fatty compound is linolenic acid (octadecatrienoic acid) and the products formed by oxidative molecular cleavage of the linolenic acid are azelaic acid (nonane-1,9-dioic acid, HOOC—(CH₂)₇—COOH), propionic acid (H₃C—CH₂—COOH) and malonic acid (HOOC—CH₂—COOH).

Advantageously and according to the invention, the fatty compound is ricinoleic acid ((9cis)-12-hydroxyoctadeca-9-enoic acid) and the products formed by oxidative molecular cleavage of the ricinoleic acid are azalaic acid (nonane-1,9-dioic acid, HOOC—(CH₂)₇—COOH), 3-hydroxynonanoic acid (HOOC—CH₂—CHOH—(CH₂)₅—CH₃).

The inventors have observed that the treatment of a hydroxylated unsaturated carboxylic acid by a method of oxidative cleavage according to the invention leads to the oxidation of the double bond but preserves the hydroxyl group.

Advantageously and according to the invention, the molar proportion of unsaturated bonds (molar equivalent number of double bonds and/or epoxide ring of the fatty compound in the emulsion) of the fatty compound and of the hydrogen peroxide introduced into the emulsion is from 1/4 to 1/10, especially approximately 1/5.

Advantageously and according to the invention, the molar proportion of unsaturated bonds (molar equivalent number of double bonds and/or epoxide ring of the fatty compound in the emulsion) of the fatty compound and of the tungstophosphoric acid introduced into the emulsion is from 1% to 5%.

Advantageously and according to the invention, the tungstophosphoric acid and the quaternary ammonium introduced into the emulsion have an equimolar proportion in the emulsion.

Advantageously and according to the invention, the oxidative molecular cleavage of the fatty compound is carried out at a temperature of from 60° C. to 120° C., especially from 70° C. to 100° C., preferably from 80° C. to 90° C.

Advantageously and according to the invention, at the end of the oxidative molecular cleavage of the fatty compound, the phase-transfer catalyst is recovered by filtration—under cold conditions at a temperature below +4° C.—and said catalyst is used in a subsequent step of oxidative molecular cleavage of a second fatty compound. Advantageously, the second fatty compound is identical to or different from the fatty compound.

The invention relates also to a method characterized in combination by all or some of the features mentioned hereinabove or hereinbelow.

Other objects, features and advantages of the invention will become apparent upon reading the following examples, which are given solely by way of a non-limiting description.

EXAMPLE 1

In Situ Preparation of the Phase-Transfer Catalyst

In a method of oxidative molecular cleavage of a fatty compound and of preparation of carboxylic acids (especially azelaic acid (COOH—$(CH_2)_7$—COOH) and pelargonic acid ($CH_3$—$(CH_2)_7$—COOH)) according to the invention, a fatty acid composition comprising oleic acid is first prepared from a sunflower oil having a high content of oleic acid (ARTERRIS, Toulouse, France). Enzymatic hydrolysis of the sunflower oil is carried out, during which 22.5 kg of sunflower oil are placed in contact with a solution of a lipase (Lyven, Colombelles, France) of *Candida cylindracea* in distilled water (20.1 kg) with magnetic stirring at 40° C. for 5 hours. A fatty acid preparation is formed, the composition of which, determined by gas chromatography, is given in Table 1 below.

TABLE 1

| Fatty acid | Composition by mass, % |
|---|---|
| Oleic acid, $C_{18:1}$ | 87.6 |
| Linoleic acid, $C_{18:2}$ | 4.7 |
| Palmitic acid, $C_{16:0}$ | 3.5 |
| Stearic acid, $C_{18:0}$ | 3.1 |
| Capric acid, $C_{10:0}$ | 0.2 |
| Others | 0.9 |

21 g of this fatty acid preparation comprising 65 mmol of oleic acid are placed in a 250 ml three-necked round-bottomed flask equipped with a cooler, a mechanical stirrer and a heating device. There are added dropwise 2 ml of an aqueous solution of a quaternary ammonium salt (3.36 mmol) selected from the group formed of tetrabutylammonium chloride (n-$Bu_4$NCl, Sigma Aldrich, Saint-Quentin Fallavier, France), tetrabutylammonium bromide (n-$Bu_4$NBr, Sigma Aldrich, Saint-Quentin Fallavier, France), N-cetylpyridinium chloride monohydrate ($C_5H_5N$(n-$C_{16}H_{33}$)$_3$Cl, $H_2O$, Sigma Aldrich, Saint-Quentin Fallavier, France), N-methyl-N,N,N-trioctylammonium chloride ($CH_3$N(n-$C_8H_{17}$)$_3$Cl, Sigma Aldrich, Saint-Quentin Fallavier, France), which is better known by the name "aliquat 336", and N,N,N,N-tetraoctylammonium chloride (N(n-$C_8H_{17}$)$_4$Cl, Sigma Aldrich, Saint-Quentin Fallavier, France). An emulsion of the oleic acid and the solution of the quaternary ammonium salt is formed by mechanical stirring of the resulting mixture.

There are prepared by mixing and stirring at ambient temperature for 30 minutes 4 g (1.2 mmol) of tungstophosphoric acid ($H_3PW_{12}O_{40}.15.4H_2O$) and 34 ml of 30% oxygenated water (325.0 mmol) in 5 ml of distilled water. The solution of tungstophosphoric acid is added to the emulsion of the oleic acid and the quaternary ammonium salt. The addition of the solution of tungstophosphoric acid to the three-necked flask containing the emulsion is carried out dropwise over a period of 5 minutes. After addition of the solution of tungstophosphoric acid to the emulsion, the reaction mixture is heated to a temperature of 60° C. The reactor is placed and maintained under mechanical stirring (400 rpm) at a temperature of 85° C. and at atmospheric pressure for a period of 5 hours, and the reactor is then allowed to cool to ambient temperature again. The pH of the reaction mixture is adjusted to a value of pH=1 by addition of one volume of an aqueous solution of hydrochloric acid at a concentration of 4 mol/l.

In order to separate the carboxylic acids formed and the catalyst, one volume of ethyl acetate is added to the acidic mixture at pH=1 and then the reaction mixture is placed at a precipitation temperature ($T_{precip}$, ambient temperature or temperature below 4° C.) so as to form a precipitate of the catalyst. The precipitate formed is washed with ethyl acetate. The aqueous phase containing the salts is separated from the organic phase in a separating funnel and is then washed with ethyl acetate. The different organic phases are combined, dried over ammonium sulfate and evaporated under reduced pressure.

The samples obtained are analyzed and quantified by gas chromatography by means of a Varian chromatograph coupled to a flame ionization detector (FID) and equipped with a capillary column (L 50 m, Ø 0.25 mm, particle size 25 µm) for analysis of the fatty acid methyl esters. The mobile phase is helium (Air liquide, France) at a pressure of 1034 hPa (15 psi) at the head of the capillary column. The temperature of the injector and of the detector is 250° C. The temperature of the oven containing the column is maintained at 100° C. for 5 minutes and is then increased gradually to 180° C. at a rate of 5° C./minute over 10 minutes and is finally increased gradually to 250° C. at a rate of 10° C./minute over 5 minutes and maintained at that temperature for 43 minutes.

For the purposes of analysis, a solution of each sample is prepared at a concentration of 10 mg/ml in methyl tert-butyl ether (MTBE). The fatty acids are converted into methyl esters by treatment with trimethylsulfonium hydroxide. Pentadecanoic acid at a concentration of 2 mg/ml is added as internal standard. The results are presented in Table 2 below, in which $T_{precip}$ is the precipitation temperature, AZA % and PEA % represent the value of the synthesis and extraction yield of azelaic acid and pelargonic acid, respectively, relative to the starting oleic acid.

TABLE 2

| Catalyst prepared in situ | $T_{precip}$ | AZA, % | PEA, % |
|---|---|---|---|
| (n-$Bu_4$N)$_3${$PO_4$[$WO(O_2)_2$]$_4$}; (A) | 4° C. | 77.6 | 80.9 |
| (n-$Bu_4$N)$_3${$PO_4$[$WO(O_2)_2$]$_4$}; (A) | RT | 72.9 | 73.9 |
| ($C_5H_5$N(n-$C_{16}H_{33}$))$_3${$PO_4$[$WO(O_2)_2$]$_4$}; (B) | 4° C. | 81.5 | 86.1 |
| ($C_5H_5$N(n-$C_{16}H_{33}$))$_3${$PO_4$[$WO(O_2)_2$]$_4$}; (B) | RT | 71.8 | 70.9 |
| ($CH_3$N(n-$C_8H_{17}$)$_3$)$_3${$PO_4$[$WO(O_2)_2$]$_4$}; (C) | 4° C. | 78.5 | 82.0 |
| ($CH_3$N(n-$C_8H_{17}$)$_3$)$_3${$PO_4$[$WO(O_2)_2$]$_4$}; (C) | RT | 71.3 | 77.2 |
| ((n-$C_8H_{17}$)$_4$N)$_3${$PO_4$[$WO(O_2)_2$]$_4$}; (D) | 4° C. | 73.2 | 76.5 |

An improved yield is observed for a precipitation of the catalyst carried out at a temperature of +4° C. in comparison with a precipitation of the catalyst carried out at ambient temperature.

EXAMPLE 2

Comparative Test—Preparation of the Phase-Transfer Catalyst in Advance

Catalysts (A) and (B) described in Example 1 are prepared in advance by a method known per se to the person skilled in the art. In particular, such a method is described in (Pai et al., (2005), Russian Chemical Bulletin, 54; 8, 1847-1854). In such a method, a 30% solution of hydrogen peroxide ($H_2O_2$) (34 ml, 325 mmol) is added to a solution of tungstophosphoric acid ($H_3PW_{12}O_{40}.15.4H_2O$, 4 g, 1.2 mmol), and the mixture is stirred for 30 minutes. An aqueous solution of 2 ml of a quaternary ammonium salt (3.36 mmol) selected from the group formed of tetrabutylammonium chloride (n-$Bu_4$NCl, Sigma Aldrich, Saint-Quentin Fallavier, France) and N-cetylpyridinium chloride monohydrate ($C_5H_5N(n-C_{16}H_{33})_3Cl$, $H_2O$, Sigma Aldrich, Saint-Quentin Fallavier, France) is added. The solid precipitate so formed is filtered off and washed with water.

A quantity of the catalyst formed above and oleic acid (21 g, 65 mmol) are mixed in a 250 ml three-necked round-bottomed flask equipped with a cooler, a mechanical stirrer and a heating device. The mixture is heated to 60° C., and a solution of hydrogen peroxide ($H_2O_2$, 325 mmol) is added dropwise over a period of 5 minutes. The reaction mixture is heated to 85° C. and maintained at atmospheric pressure for 5 hours with magnetic stirring (400 rpm). The reactor is allowed to cool to ambient temperature. The reaction mixture is then treated and analyzed as in Example 1. The results of the analyses are shown by way of comparison in Table 3 below.

TABLE 3

| Catalyst | $T_{precip}$ | AZA, % | PEA, % |
|---|---|---|---|
| $(n-Bu_4N)_3\{PO_4[WO(O_2)_2]_4\}$; (A) | 4° C. | 52.0 | 57.1 |
| $(C_5H_5N(n-C_{16}H_{33}))_3\{PO_4[WO(O_2)_2]_4\}$; (B) | 4° C. | 70.2 | 75.1 |

An improved yield of the conversion reaction of oleic acid to azelaic acid and pelargonic acid is observed for the synthesis carried out by in situ formation of the catalyst (Table 2).

With catalyst (A) and treatment at 4° C., the yield of the reaction increases from a value of 52% (azelaic acid) and 57.1% (pelargonic acid) for preparation of the catalyst in advance (Table 3) to a value of 77.6% (azelaic acid) and 80.9% (pelargonic acid) for in situ synthesis of the catalyst (Table 2), that is to say an increase of over 40%. With catalyst (B) and treatment at 4° C., the yield of the reaction increases from a value of 70.2% (azelaic acid) and 75.1% (pelargonic acid) for preparation of the catalyst in advance (Table 3) to a value of 81.5% (azelaic acid) and 86.1% (pelargonic acid) for in situ synthesis of the catalyst (Table 2), that is to say an increase of approximately 15%.

EXAMPLE 3

Selection of the Quaternary Ammonium Salt

An oxidative molecular cleavage of oleic acid as described in Example 1 is carried out, in which the molar proportions of the reagents are:
oleic acid: 1 equivalent
$H_2O_2$: 5 equivalents
catalyst formed in situ: 0.02 equivalent.

The reaction mixture is heated to 85° C. and maintained at atmospheric pressure for 5 hours with mechanical stirring (400 rpm). For the in situ preparation of the catalyst, the quaternary ammonium salt described in Table 4 below is selected. The column "OLA %" represents the molar fraction of oleic acid converted in the reaction.

TABLE 4

| Ammonium salt | $X^-$ | OLA, % | AZA, % | PEA, % |
|---|---|---|---|---|
| None | — | 38.1 | 1.8 | 2.2 |
| $(n-Bu_4N)^+X^-$ | $Cl^-$ | 100 | 77.6 | 80.9 |
| $(n-Bu_4N)^+X^-$ | $Br^-$ | 100 | 71.8 | 76.2 |
| $C_5H_5N(n-C_{16}H_{33})^+X^-$ | $Cl^-$ | 100 | 81.5 | 86.1 |
| $CH_3N(n-C_8H_{17})_3^+X^-$ | $Cl^-$ | 100 | 75.7 | 80.7 |
| $N(n-C_8H_{17})_4^+X^-$ | $Cl^-$ | 100 | 73.2 | 76.5 |

In the absence of catalyst, 38.1% of the starting oleic acid disappears and permits the formation of many products, of which only 1.8% azelaic acid and 2.2% pelargonic acid.

The in situ formation of catalysts starting from the ammonium salts $(n-Bu_4N)^+Cl^-$, $(n-Bu_4N)^+Br^-$, $C_5H_5N(n-C_{16}H_{33})^+Cl^-$, $CH_3N(n-C_8H_{17})_3^+Cl^-$ and $N(n-C_8H_{17})_4^+Cl^-$ allows 100% of the starting oleic acid to be converted and azelaic acid and pelargonic acid to be formed with a yield greater than 73% for azelaic acid and greater than 76% for pelargonic acid.

EXAMPLE 4

Effect of the Temperature

A treatment of oxidative molecular cleavage of oleic acid as described in Example 1 is carried out, in which one of the catalysts (A), (B), (C) or (D) is formed in situ and the synthesis is carried out at a temperature $T_{reaction}$ specified in Table 5 below and in which the value "OLA %" represents the molar fraction of oleic acid converted in the reaction, "AZA %" and "PEA %" represent the value of the synthesis and extraction yield of azelaic acid and pelargonic acid, respectively, relative to the starting oleic acid.

TABLE 5

| Catalyst prepared in situ | $T_{reaction}$, ° C. | OLA % | AZA % | PEA % |
|---|---|---|---|---|
| $(n-Bu_4N)_3\{PO_4[WO(O_2)_2]_4\}$; (A) | 75 | 100 | 59.2 | 66.5 |
| (A) | 85 | 100 | 77.6 | 80.9 |
| (A) | 95 | 99.5 | 65.8 | 73.3 |
| $(C_5H_5N(n-C_{16}H_{33}))_3\{PO_4[WO(O_2)_2]_4\}$; (B) | 65 | 96.6 | 40.8 | 44.2 |
| (B) | 75 | 100 | 66.8 | 71.1 |
| (B) | 85 | 100 | 81.5 | 86.1 |
| (B) | 95 | 100 | 77.6 | 80.2 |
| (B) | 105 | 99.3 | 60.9 | 60.5 |
| $(CH_3N(n-C_8H_{17})_3)_3\{PO_4[WO(O_2)_2]_4\}$; (C) | 75 | 100 | 69.2 | 74.8 |
| (C) | 85 | 100 | 75.7 | 80.7 |
| (C) | 95 | 99.8 | 78.5 | 82.0 |
| (C) | 105 | 100 | 71.5 | 76.1 |
| (C) | 115 | 100 | 72.8 | 77.2 |

The best yields are obtained at a temperature of approximately 85° C. for catalysts (A) and (B) and of approximately 95° C. for catalyst (C).

EXAMPLE 5

Proportion of Catalyst

A treatment of oxidative molecular cleavage of oleic acid as described in Example 1 is carried out, in which catalyst (B) is formed in situ in a molar proportion specified in Table 6 below and in which the value "OLA %" represents the molar fraction of oleic acid converted in the reaction, "AZA %" and "PEA %" represent the value of the synthesis yield of azelaic acid and pelargonic acid, respectively, relative to the starting oleic acid. The initial quantity of oleic acid (OLA) is 65 mmol and the initial quantity of $H_2O_2$ is 325 mmol (30%). The initial molar ratio OLA/$H_2O_2$ is 1/5, the temperature is 85° C., the reaction time is 5 hours and the stirring speed is 400 rpm.

TABLE 6

| Catalyst (B) prepared in situ $(C_5H_5N(n\text{-}C_{16}H_{33}))_3\{PO_4[WO(O_2)_2]_4\}$ mol % relative to OLA | OLA % | AZA % | PEA % |
|---|---|---|---|
| 1 | 100 | 69.3 | 68.3 |
| 2 | 100 | 81.5 | 86.1 |
| 4 | 100 | 70.9 | 62.3 |

The molar proportion of catalyst formed in situ that allows the best yield to be obtained is approximately 2%.

EXAMPLE 6

Stirring Speed

A treatment of oxidative molecular cleavage of oleic acid as described in Example 1 is carried out, in which catalyst (B) is formed in situ in a molar proportion of 2%. The initial quantity of oleic acid (OLA) is 65 mmol and the initial quantity of $H_2O_2$ is 325 mmol (30%). The initial molar ratio OLA/$H_2O_2$ is 1/5, the temperature is 85° C., the reaction time is 5 hours and the speed of rotation of the mechanical stirrer is from 250 rpm to 1250 rpm.

A reduction in the synthesis yield of azelaic acid and pelargonic acid is observed for a speed of rotation of the mechanical stirrer greater than 800 rpm. The inventors suppose that a speed of rotation of the mechanical stirrer greater than 800 rpm is likely to allow air bubbles to be introduced into the reaction mixture by cavitation and the contact area between the catalyst and the substrate to be reduced.

In addition, a reduction in the yield is also observed for a speed of rotation of the mechanical stirrer below 300 rpm. The inventors suppose that such a speed of rotation of the mechanical stirrer below 300 rpm is insufficient to allow the formation of an emulsion between the oleic acid and the oxidizing agent ($H_2O_2$) and results in a reduction in the yield.

EXAMPLE 7

Oxidative Cleavage of 9,10-Epoxyoctadecanoic Acid 9,10-Epoxyoctadecanoic acid is prepared according to a method described in "Salimon et al., (2009), European Journal of Scientific Research, 32(2), 216-222" and in which 71 mmol of oleic acid are treated with freshly prepared performic acid at ambient temperature for 3 hours with magnetic stirring (400 rpm). A white powder of 9,10-epoxyoctadecanoic acid (51 mmol) is obtained, with a degree of purity of 65% and a yield of 72%.

A treatment of oxidative molecular cleavage of the 9,10-epoxyoctadecanoic acid is carried out, in which catalyst (B) is formed in situ in a molar proportion of 2%. The initial quantity of 9,10-epoxyoctadecanoic acid is 51 mmol and the initial quantity of $H_2O_2$ is 255 mol (30%). The initial molar ratio 9,10-epoxyoctadecanoic acid/$H_2O_2$ is 1/5, the temperature is 85° C., the reaction time is 5 hours and the speed of rotation of the mechanical stirrer is 400 rpm.

The rate of conversion "TC" of 9,10-epoxyoctadecanoic acid, "AZA %" and "PEA %", which represent the value of the synthesis yield of azelaic acid and pelargonic acid, respectively, relative to the starting 9,10-epoxyoctadecanoic acid, are given in Table 7 below.

TABLE 7

| Catalyst (B) prepared in situ | TC, % | AZA % | PEA % |
|---|---|---|---|
| $(C_5H_5N(n\text{-}C_{16}H_{33}))_3\{PO_4[WO(O_2)_2]_4\}$ | 98.9 | 86.5 | 87.3 |

EXAMPLE 8

Oxidative Cleavage of Linoleic Acid (LNA)

A treatment of oxidative molecular cleavage of linoleic acid ((9cis,12cis)-octadeca-9,12-dienoic acid, LNA) is carried out according to tests no. 1 and no. 2, in which catalyst (B) is formed in situ in linoleic acid (LNA). The molar proportion LNA/$H_2O_2$/catalyst is specified in Table 8 below. The value "LNA %" represents the molar fraction of linoleic acid converted in the reaction. The values "HA %" and "AZA %" represent the value of the synthesis and extraction yield of the hexanoic monoacid (HA) and the azelaic diacid (AZA), respectively, relative to the starting linoleic acid (LNA). The temperature is 85° C., the reaction time is 5 hours and the stirring speed is 400 rpm.

TABLE 8

|  | Test no. 1 | Test no. 2 |
|---|---|---|
| LNA, mmol | 60 | 22 |
| $H_2O_2$, mmol | 350 | 220 |
| LNA/$H_2O_2$ | 1/5.8 | 1/10 |
| Cat (B), mmol | 1.2 | 0.9 |
| LNA/Cat (B) | 1/50 (0.02%) | 1/25 (0.04%) |
| LNA % | 100 | 100 |
| HA % | 47.7 | 60.7 |
| AZA % | 41.0 | 49.8 |

EXAMPLE 9

Oxidative Cleavage of Ricinoleic Acid

A treatment as described in Example 1 of oxidative molecular cleavage of ricinoleic acid (or (9cis)-12-hydroxy-octadeca-9-enoic acid) obtained from the hydrolysis of castor oil is carried out, in which catalyst (B) is formed in situ in a molar proportion of 2%. The initial quantity of ricinoleic acid is 14 mmol and the initial quantity of $H_2O_2$ is 163 mmol (30%).

The temperature is 85° C., the reaction time is 5 hours and the stirring speed is 400 rpm.

The oxidative molecular cleavage of the ricinoleic acid leads to the formation of a diacid (azelaic acid, AZA) and of a monoacid (3-hydroxynonanoic acid), which are extracted in ethyl acetate.

Azelaic acid and 3-hydroxynonanoic acid are obtained with yields of 83.2% and 60.8%, respectively, for a rate of conversion of ricinoleic acid of 99.9%.

The invention claimed is:
1. A method of oxidative molecular cleavage of a fatty compound selected from the group formed of unsaturated aliphatic carboxylic acids, esters of an unsaturated aliphatic carboxylic acid, epoxidized aliphatic carboxylic acids, esters of an epoxidized aliphatic carboxylic acid, hydroxylated unsaturated aliphatic carboxylic acids, and esters of a hydroxylated unsaturated aliphatic carboxylic acid, wherein:
a composition, called a fatty composition, composed of at least one aliphatic carboxylic acid is formed, said fatty composition comprising the fatty compound;
which method comprises:
subsequently adding to said fatty composition a solution of at least one quaternary ammonium salt in water capable of forming an emulsion of said fatty compound and water; and then
adding to said emulsion a liquid solution of at least one tungstophosphoric acid in a composition comprising hydrogen peroxide ($H_2O_2$),
so as to form in situ in the emulsion a quantity of a catalyst, called a phase-transfer catalyst, formed of tungstophosphoric acid and at least one quaternary ammonium of the quaternary ammonium salt(s), and to permit the oxidative molecular cleavage of the fatty compound.

2. The method as claimed in claim 1, wherein the fatty compound is selected from the group formed of the fatty compounds of the following general formula (II):

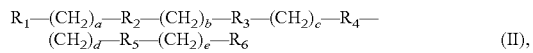  (II), wherein:
$R_1$ and $R_6$ are two identical or different groups of atoms selected from a methyl ($-CH_3$) and a carboxyl ($-COOH$) and an ester group of the general formula $-COOR_7$ wherein $R_7$ is a linear aliphatic hydrocarbon group containing from 1 to 8 carbon atoms;
$R_2$, $R_3$, $R_4$ and $R_5$ are identical or different groups of atoms selected from a group $-CH_2-$, an epoxide group

and a group ($-CH=CH-$);
a, b, c, d and e are identical or different natural integers of the interval [0; 15].

3. The method as claimed in claim 1, wherein each quaternary ammonium salt is selected from the group formed of the quaternary ammonium salts of the following general formula (III):

$$A_1A_2A_3A_4N^+X^- \quad (III),$$

wherein:
$A_1$, $A_2$, $A_3$ and $A_4$ are identical or different aliphatic hydrocarbon groups having a number of carbon atoms of less than 10; and
$X^-$ is an anion.

4. The method as claimed in claim 1, wherein the fatty composition is free of organic solvent.

5. The method as claimed in claim 1, wherein the fatty compound is oleic acid ((9cis)-octadec-9-enoic acid) and wherein the products formed are azelaic acid (HOOC—$(CH_2)_7$—COOH) and pelargonic acid ($H_3C$—$(CH_2)_7$—COOH).

6. The method as claimed in claim 1, wherein the fatty compound is linoleic acid ((9cis,12cis)-octadeca-9,12-dienoic acid) and wherein the products formed by oxidative molecular cleavage of the linoleic acid are azelaic acid (HOOC—$(CH_2)_7$—COOH), malonic acid (HOOC—$CH_2$—COOH) and hexanoic acid ($H_3C$—$(CH_2)_4$—COOH).

7. The method as claimed in claim 1, wherein the fatty compound is 9,10-epoxyoctadecanoic acid and wherein the products formed by oxidative molecular cleavage of the 9,10-epoxyoctadecanoic acid are azelaic acid (HOOC—$(CH_2)_7$—COOH) and pelargonic acid ($H_3C$—$(CH_2)_7$—COOH).

8. The method as claimed in claim 1, wherein the fatty compound is arachidonic acid and wherein the products formed by oxidative molecular cleavage of the arachidonic acid are hexanoic acid ($H_3C$—$(CH_2)_4$—COOH), malonic acid (HOOC—$CH_2$—COOH) and pentanedioic acid (HOOC—$(CH_2)_3$—COOH).

9. The method as claimed in claim 1, wherein the fatty compound is linolenic acid and wherein the products formed by oxidative molecular cleavage of the linolenic acid are azelaic acid (HOOC—$(CH_2)_7$—COOH), propionic acid ($H_3C$—$CH_2$—COOH) and malonic acid (HOOC—$CH_2$—COOH).

10. The method as claimed in claim 1, wherein the molar proportion of the unsaturated bonds of the fatty compound and of the hydrogen peroxide introduced into the emulsion is from 1/4 to 1/10.

11. The method as claimed in claim 1, wherein the molar proportion of the unsaturated bonds of the fatty compound and of the tungstophosphoric acid introduced into the emulsion is from 1% to 5%.

12. The method as claimed in claim 1, wherein the tungstophosphoric acid and the quaternary ammonium introduced into the emulsion have an equimolar proportion in the emulsion.

13. The method as claimed in claim 1, wherein the oxidative molecular cleavage of the fatty compound is carried out at a temperature of from 60° C. to 120° C.

14. The method as claimed in claim 1, wherein, at the end of the oxidative molecular cleavage of the fatty compound, the phase-transfer catalyst is recovered by filtration and said phase-transfer catalyst is used in a subsequent step of oxidative molecular cleavage of a second fatty compound.

15. The method as claimed in claim 2, wherein each quaternary ammonium salt is selected from the group formed of the quaternary ammonium salts of the following general formula (III):

  (III), wherein:
$A_1$, $A_2$, $A_3$ and $A_4$ are identical or different aliphatic hydrocarbon groups having a number of carbon atoms of less than 10; and
$X^-$ is an anion.

* * * * *